United States Patent
Wallin

(10) Patent No.: US 7,036,513 B2
(45) Date of Patent: May 2, 2006

(54) BARRIER DEVICE

(75) Inventor: Lars G. Wallin, Laholm (SE)

(73) Assignee: Sileco HB, Laholm (SE)

( * ) Notice: Subject to any disclaimer, the term of this patent is extended or adjusted under 35 U.S.C. 154(b) by 210 days.

(21) Appl. No.: 10/492,521

(22) PCT Filed: Apr. 11, 2002

(86) PCT No.: PCT/SE02/00713

§ 371 (c)(1),
(2), (4) Date: Apr. 14, 2004

(87) PCT Pub. No.: WO02/085233

PCT Pub. Date: Oct. 31, 2002

(65) Prior Publication Data

US 2004/0231677 A1  Nov. 25, 2004

(30) Foreign Application Priority Data

Apr. 11, 2001  (SE)  ................................ 0101305

(51) Int. Cl.
*A61B 19/00* (2006.01)
*A61F 5/37* (2006.01)

(52) U.S. Cl. .................. 128/849; 128/851; 128/853; 128/855

(58) Field of Classification Search ............. 128/849, 128/850, 851, 852, 853, 854, 855, 856, 857, 128/888; 602/41
See application file for complete search history.

(56) References Cited

U.S. PATENT DOCUMENTS

| 3,561,440 A | * | 2/1971 | Bayer et al. ............... 128/853 |
| 3,871,369 A |   | 3/1975 | Krzewinski |
| 4,524,767 A | * | 6/1985 | Glassman ................... 128/854 |
| 4,561,434 A | * | 12/1985 | Taylor ....................... 128/849 |
| 5,713,372 A | * | 2/1998 | Pinney et al. ............... 128/855 |
| 5,765,566 A | * | 6/1998 | Rothrum ................... 128/849 |
| 6,199,553 B1 | * | 3/2001 | Hafer et al. ............... 128/849 |
| 2003/0121522 A1 | * | 7/2003 | Gingles et al. ........... 128/853 |

FOREIGN PATENT DOCUMENTS

| EP | 0 619 099 |   | 10/1994 |
| WO | WO 98/22037 | * | 2/1998 |

* cited by examiner

Primary Examiner—Henry Bennett
Assistant Examiner—Amanda Wieker
(74) Attorney, Agent, or Firm—Buchanan Ingersoll PC

(57) ABSTRACT

A barrier device for applying a surgical cloth adjacent to the location on a patient's body where a surgical intervention is to be performed, the barrier device having an upper side of which a part is intended to abut against the underside of the surgical cloth. An underside is intended to abut against the patient's skin. The barrier device has a front edge and a rear edge near and at a distance from, respectively, the location on the patient's body where the surgical intervention is to be performed. The barrier device is on its underside at the front edge provided with a first adhesive portion, and on its upper side provided with a protruding, elongate and flexible fastening flap which on the side facing the rear edge is provided with a second adhesive portion for adhesion to the surgical cloth.

20 Claims, 1 Drawing Sheet

BARRIER DEVICE

FIELD OF THE INVENTION

The present invention relates to a barrier device for applying a surgical cloth adjacent to the location on a patient's body where a surgical intervention is to be performed, the barrier device having an upper side of which one part is intended to abut against the underside of the surgical cloth, an underside intended to abut against the patient's skin, and a front edge and a rear edge near and at a distance from, respectively, the location on the patient's body where the surgical intervention is to be performed, and to a method for pre-operative preparation of a surgical cloth.

BACKGROUND ART

In connection with different types of surgical interventions it is always important to prevent infections as far as possible, which can be made in different ways. In the usual procedure, the surgical area on the patient's body is first disinfected with alcohol or some other disinfectant. Subsequently, the patient is dressed in surgical cloths and sheets. Moreover, the operating personnel work in sterile overalls, protective masks and sterile gloves.

The surgical cloths having so-called barriers against contaminating material are today available in essentially two embodiments. One variant consists of non-disposable material of polyester and/or cotton with an intermediate plastic sheeting barrier. The textile fabric serves as an absorbent, while the plastic constitutes a fluid barrier. The surgical cloth is attached to the patient's skin by detachable pieces of tape. One disadvantage of this variant is that it is difficult to see if the tape pieces are properly attached to the skin, which otherwise would result in a risk of leakage. In addition, there is a risk of bacteria, viruses and other contaminants migrating, or even migrating back, from the surgical cloth and into the surgical area, i.e. the location on the patient's body where the surgical intervention is to be performed.

The second and most frequent variant is disposable laminate consisting of non-woven and plastic sheeting having an edge fitted with tape. The non-woven material constitutes an absorbent, while the plastic serves as a barrier against contaminants. The disadvantages of this variant are that it must be disposed of after having been used only once, that it is difficult to see with the eye if the edge fitted with tape is properly attached to the skin, that the non-woven material may have been delaminated, that wet non-woven material may detach itself, for example, when gloves and sleeves are drawn to it and that it is difficult to attach surgical cloths overlapping one another since tape adheres unsatisfactorily to nonwoven.

SUMMARY OF THE INVENTION

One object of the present invention is thus to solve the above-mentioned problems by providing an improved barrier device for surgical cloths. According to the invention, this object is achieved by means of a barrier device of the type stated by way of introduction and having the features which will be evident from claim 1. Preferred embodiments are stated in the subclaims. The object is also achieved by a method for pre-operative preparation of a surgical cloth as claimed in claim 11.

BRIEF DESCRIPTION OF THE DRAWING

In the following, the invention will be further described in more detail with reference to the accompanying drawing.

DESCRIPTION OF A PREFERRED EMBODIMENT

In the following, a preferred embodiment of the present invention, but also other embodiments thereof, will be described with reference to the accompanying drawing.

The expression "surgical cloth" used in the application text relates to the absorbing textile fabric to which the barrier device according to the present invention is intended to be attached.

Figure 1:
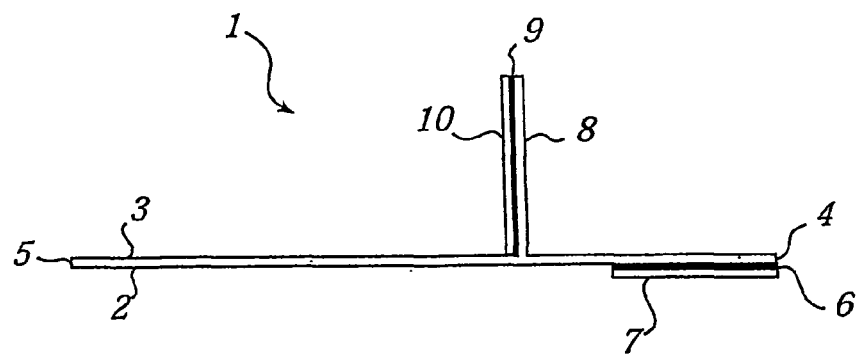
FIG. 1 is a side view of a barrier device according to one embodiment of the invention.

As shown in FIG. 1, the barrier device 1 according to the present invention has on its underside 2 at its front edge 4 a first adhesive portion 6. The first adhesive portion 6 is preferably covered by a first release layer 7. On the upper side 3 of the barrier device 1 there is also a longitudinal fastening flap 8 which on the side facing the rear edge 5 of the barrier device 1 has a second adhesive portion 9, which preferably is covered by a second release layer 10. The second adhesive portion 9 constitutes the entire or part of the above-mentioned side of the fastening flap 8, preferably at least that part of the side in question which is found at the upper free end of the fastening flap 8, and runs in the longitudinal direction of the whole fastening flap 8.

Figure 2:
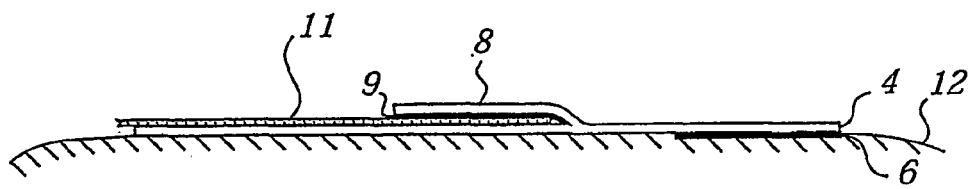
FIG. 2 is a side view of a surgical cloth provided with a barrier device according to the present invention attached to a patient's skin.
Figure 3:
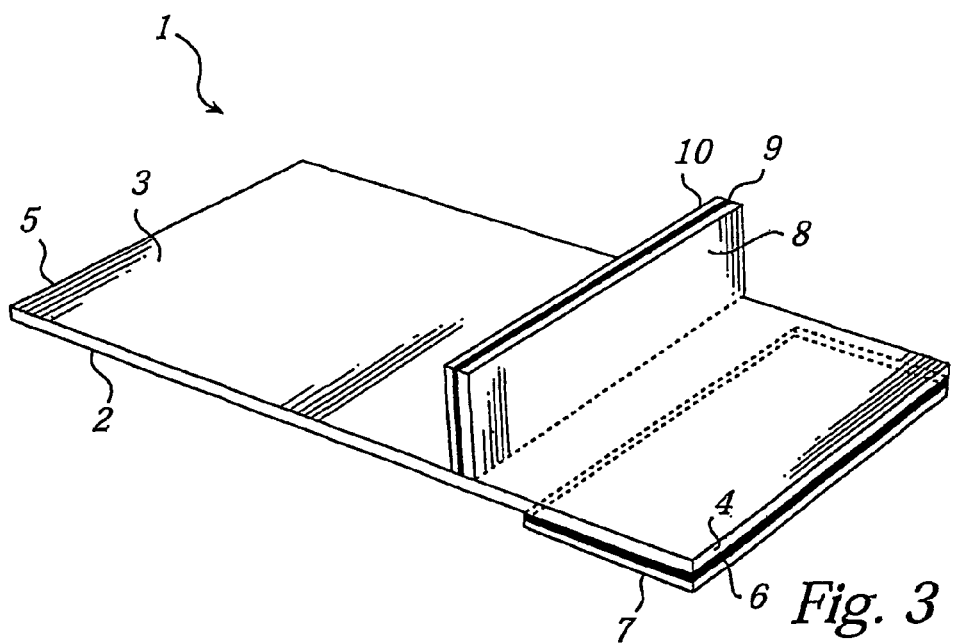
FIG. 3 is a perspective view of a barrier device according to one embodiment of the present invention.

In pre-operative preparation of a surgical cloth 11, it is placed on the part of the upper side 3 of the barrier device 1 between the fastening flap 8 and the rear edge 5. The second release layer 10 on the fastening flap 8 is removed, after which the fastening flap 8 is folded over the edge of the surgical cloth 11. The fastening flap 8 is attached to the surgical cloth 11 by means of the second adhesive portion 9. Consequently, a fluid-tight encapsulation of the edge of the surgical cloth 11 is provided. This reduces the risk of bacteria, viruses and other contaminants being transported into the surgical area. Moreover, the exsudate (the fluid or the impurities coming from an operation wound) is stored farther away from the surgical area, which further reduces the risk of infection. The surgical cloth 11 provided with the barrier device 1 is sterilised, preferably by curing with high-pressure steam. When a surgical cloth 11 is to be applied on a patient, the first release layer 7 is removed from the first adhesive portion 6, after which the first adhesive portion 6 is accurately applied on the patient's skin 12 in a fluid-tight manner as shown in FIG. 2.

In one embodiment, the barrier device 1 has a size of about 1×1 m and is preferably made of a flexible and liquid-tight plastic material which can resist curing with high-pressure steam at 134° C. and which does not let through viruses and bacteria. A suitable material is coextruded polyethylene and polypropylene. The first adhesive portion 6 is transparent, which implies that it is easy to control that the surgical cloth 11 is properly attached to the patient's skin 12, which has not been possible earlier when using existing products. Thus, unnecessary pressing with one's fingers on the patient to establish sealing is avoided. The first adhesive portion 6 is preferably made of polypropylene, polyester, polyurethane or some other liquid-tight material and is provided with an adhesive composition, preferably polyacrylate, that is kind to the skin. Advantageously, the first adhesive portion 6 is also micro-embossed for eliminating undesirable reflections from localised work illumination in surgical operations. The fastening flap 8 is made of a flexible material, e.g. polypropylene, and is preferably micro-embossed. The second adhesive portion 9 is provided with an adhesive material that adheres well to fabrics. In a preferred embodiment, the fastening flap is about 5 cm high, but can also be higher or lower as long as it allows satisfactory adhesion to the surgical cloth.

In an alternative embodiment, the fastening flap 8 is not provided with a second adhesive portion 9. Instead a separate piece of tape is used to attach the fastening flap 8 to the surgical cloth 11.

In a preferred embodiment, the first adhesive portion 6 extends to a width of about 5 cm seen from the front edge 4, but can also extend further in the direction of the rear edge 5 on the underside 2 of the barrier device 1, even past the line along which the fastening flap 8 runs. Furthermore, the first adhesive portion 6 extends in the longitudinal direction parallel to and along the entire front edge 4. Thus, the front edge 4 can be sealingly attached to the patient's skin along its whole length. Preferably, the fastening flap 8 runs parallel to the front edge 4, but can also be inclined relative to the same. The front edge 4 can be straight as well as bent, or shaped in some other irregular way, as long as the first adhesive surface 6 can be attached in a simple and sealing manner. The dimensions of the barrier device can, of course, be adapted to the size of the surgical cloth desirable to use, and to the appearance of the surgical area on the patient that is to be delimited.

The first and the second release layers (7, 10) which before use of the barrier device 1 according to the present invention preferably are positioned on the first and the second adhesive portions (6, 9), respectively, are usually made of siliconised paper.

The thickness of the barrier device 1 including the fastening flap 8 is not critical as long as the device and the parts thereof are flexible enough in order to fulfil their purposes. Thus, it should be possible to carry out the application on the patient smoothly, and to easily fold the fastening flap 8 and attach it to the surgical cloth. Preferably, the barrier device 1 consists of a thin film.

The plasticised edge on the surgical cloth 11 also makes it easy to attach several overlapping surgical cloths 11 by means of an adhesive composition in such a manner that a completely tight square or rectangle is formed round the surgical area. The fact is that the first adhesive portion 6 adheres most satisfactorily to the plastic upper side of the folded and fixed fastening flap 8.

Yet another advantage of the present invention is that the plastic strip under which the first adhesive portion is located can be cut through when needed and, thus, constitute a so-called incision cloth in the cases when the surgical area turns out to be larger than estimated, i.e. larger than the delimited skin area.

After use the surgical cloth 11 can easily be separated from the barrier device 1, after which the barrier device 1 only is disposed of, for example, by burning. Recycling is possible but not suitable due to the risk of infection. However, the surgical cloth 11 can be washed and reused.

Consequently, the present invention provides a resource-efficient but safe barrier device 1 of disposable type for surgical cloths 11.

It should be pointed out that the above-described components of the barrier device 1 can be made of other materials than those mentioned above as long as the requirements for tightness, flexibility, reasonable manufacturing cost and compatibility are fulfilled.

The invention claimed is:

1. A barrier device (1) for applying a surgical cloth (11) adjacent to the location on a patient's body where a surgical intervention is to be performed, the barrier device (1) having an upper side (3) of which a part is intended to abut against the underside of the surgical cloth (11), an underside (2) intended to abut against the patient's skin (12), and a front edge (4) and a rear edge (5) near and at a distance from, respectively, the location on the patient's body where the surgical intervention is to be performed, wherein the barrier device (1) on its underside (2) at the front edge (4) is provided with a first adhesive portion (6), and that the barrier device (1) on its upper side (3) is provided with a protruding, elongate arid, flexible fastening flap (8) which on the side facing the rear edge (5) is provided with a second adhesive portion (9) for adhesion to the surgical cloth.

2. A barrier device (1) as claimed in claim 1, wherein at least part of the first adhesive portion (6) is transparent.

3. A barrier device (1) as claimed in claim 2, wherein a first release layer (7) is applied on the first adhesive portion (6) with the purpose of being removed before adhesion to the patient's skin (12).

4. A barrier device (1) as claimed in claim 3, wherein a second release layer (10) is applied on the second adhesive portion (9) with the purpose of being removed before folding the fastening flap (8) for adhesion of the same to the surgical cloth (11).

5. A barrier device (1) as claimed in claim 3, wherein the main part is made of coextruded polyethylene and polypropylene.

6. A barrier device (1) as claimed in claim 2, wherein a second release layer (10) is applied on the second adhesive portion (9) with the purpose of being removed before folding the fastening flap (8) for adhesion of the same to the surgical cloth (11).

7. A barrier device (1) as claimed in claim 2, wherein the main part is made of coextruded polyethylene and polypropylene.

8. A barrier device (1) as claimed in claim 1, wherein a first release layer (7) is applied on the first adhesive portion (6) with the purpose of being removed before adhesion to the patient's skin (12).

9. A barrier device (1) as claimed in claim 8, wherein a second release layer (10) is applied on the second adhesive portion (9) with the purpose of being removed before folding the fastening flap (8) for adhesion of the same to the surgical cloth (11).

10. A barrier device (1) as claimed in claim 8, wherein the main part is made of coextruded polyethylene and polypropylene.

11. A barrier device (1) as claimed in claim 1, wherein a second release layer (10) is applied on the second adhesive portion (9) with the purpose of being removed before folding the fastening flap (8) for adhesion of the same to the surgical cloth (11).

12. A barrier device (1) as claimed in claim 11, wherein the main part is made of coextruded polyethylene and polypropylene.

13. A barrier device (1) as claimed in claim 1, wherein the main part is made of coextruded polyethylene and polypropylene.

14. A barrier device (1) as claimed in claim 1, wherein the first and the second adhesive portions (6, 9) are made of polypropylene, polyurethane or polyester.

15. A barrier device (1) as claimed in claim 1, wherein the first and the second release layers (7, 10) are made of siliconised paper.

16. A barrier device (1) as claimed in claim 1, wherein the fastening flap (8) extends essentially parallel to the front edge (4).

17. A barrier device (1) as claimed in claim 1, wherein the rear edge (5), the fastening flap (8) and the front edge (4) run parallel.

18. A barrier device (1) as claimed in claim 1, wherein a surgical cloth (11) abuts against a part of the upper side (3) and is tightly attached to the fastening flap (8) via the second adhesion portion (9) of the fastening flap (8).

19. A method for pre-operative preparation of a surgical cloth (11), comprising the steps of
placing a surgical cloth (11) in such a manner that its underside abuts against a part of the upper side (3) of a barrier device as claimed in claim 1,
uncovering the second adhesive portion (9) of the fastening flap (8) and folding the fastening flap (8) in such a manner that the second adhesive portion (9) covers the front edge of the surgical cloth (11) so that a tight seal is obtained.

20. A method as claimed in claim 19, wherein it further comprises sterilisation of the surgical cloth (11) provided with the barrier device (1) and adhesion of the same to the patient's skin (12).

* * * * *